US005601986A

United States Patent [19]
Takacs

[11] Patent Number: 5,601,986
[45] Date of Patent: Feb. 11, 1997

[54] ASSAYS AND DEVICES FOR THE DETECTION OF EXTRAHEPATIC BILIARY ATRESIA

[75] Inventor: Laszlo Takacs, Newbury Park, Calif.

[73] Assignee: Amgen Inc., Thousand Oaks, Calif.

[21] Appl. No.: 275,887

[22] Filed: Jul. 14, 1994

[51] Int. Cl.$^6$ .................................................. G01N 33/573
[52] U.S. Cl. ............................... 435/7.4; 435/24; 422/56; 436/811
[58] Field of Search ........................ 435/7.4, 24; 422/56; 436/811

[56] References Cited

U.S. PATENT DOCUMENTS

| | | | |
|---|---|---|---|
| 4,191,809 | 3/1980 | Nagatsu et al. | 435/24 |
| 4,299,916 | 11/1981 | Litman et al. | 435/6 |
| 5,122,602 | 6/1992 | Corey et al. | 536/17.2 |

OTHER PUBLICATIONS

Hutchinson, D. R. et al. Clinica Chimica Acta, 109:83–89 (1981).
Wright, K. et al. Am J DisChild, 135:134–136 (1981).
Platt, M. S. et al. Am J Dis Child, 135:834–836 (1981).
Kato, T. et al. Clin. Chem., 24(7):1163–1166 (1978).
Hauvi, H.-P. et al. J Cell Biol., 101:838–851 (1985).
Bristol, et al., "Characterization of Novel Rat Thymocyte Costimulating Antigen by the Monoclonal Antibody 1.3" *The Journal of Immunology*, vol. 148, pp. 332–338 (1992).
Bristol, et al., "Thymocyte Costimulating Antigen is CD26 (Dipeptidyl–Peptidase IV)—Costimulation of Granulocyte, Macrophage, and T Lineage Cell Proliferation Via CD26" *The Journal of Immunology*, vol. 149, pp. 367–372 (1992).

Esquivel, et al., "Indications for Pediatric Liver Transplantation", *The Journal of Pediatrics*, vol. 111, pp. 1039–1045 (1987).
Fleischer, "CD26: A Surface Protease Involved in T–Cell Activation", *Immunollogy Today*, vol. 15, pp. 180–184 (1994).
Karrer, et al., "Congenital Biliary Trac Disease", *Surgical Clinics of North America*, vol. 70, pp. 1403–1418 (1990).
Logan, et al., "Screening for Biliary Atresia", *The Lancet*, vol. 342, p. 256 (1993).
Ryckman, et al., "Neonatal Cholestatic Conditions Requiring Surgical Reconstruction", *Seminars in Liver Disease*, vol. 7, pp. 134–154 (1987).
Tagge, et al., "A Long–Term Experience with Biliary Atresia", *Ann. Surg.*, vol. 214, pp. 590–598 (1991).
Wall, et al. "Liver Transplantation: Current Concepts", *CMAJ*, vol. 139, pp. 21–28 (1988).

*Primary Examiner*—James C. Housel
*Assistant Examiner*—Theresa King
*Attorney, Agent, or Firm*—Craig A. Crandall; Daniel R. Curry; Steven M. Odre

[57] ABSTRACT

The present invention involves a variety of assay methods and devices for screening or diagnosing the occurrence of extrahepatic biliary atresia. In particular the methods and devices involve an antibody specifically for the detection of dipeptidyl peptidase IV in a test sample as indicative of extrahepatic biliary atresia.

18 Claims, 3 Drawing Sheets

ASSAYS AND DEVICES FOR THE DETECTION OF EXTRAHEPATIC BILIARY ATRESIA

FIELD OF THE INVENTION

The present invention relates to the diagnosis of extrahepatic biliary atresia. In particular, the invention involves the detection of dipeptidyl peptidase IV as an indication of the occurrence of extrahepatic biliary atresia.

BACKGROUND

Biliary atresia reflects total or partial agenesis of the biliary tree and usually affects extrahepatic, rather than intrahepatic, bile ducts. Extrahepatic biliary atresia (EHBA) is a heterogeneous, rare disease, which is fatal if untreated. The incidence of EHBA varies considerably in various geographic areas but is estimated to affect one in 18,000 live births each year in the United States alone. EHBA results from the discontinuous or failed development of bile ducts to the gut. Without the ducts, bile detergents begin to degrade the bile brush border of the bile capillary epithelium and these materials leak to the venous sinusoids of the liver, ultimately connecting to the systemic circulation. In most cases, biliary atresia develops several weeks after birth, probably following inflammation and scarring of the bile ducts. It is rarely found in still-borns or in the immediate neonatal period. The etiology of the inflammatory response is often unknown.

Affected children may appear normal at birth and are recognized due to progressive obstructive jaundice at three to six weeks of age. This course reflects the pathologic changes within the bile ducts in biliary atresia, namely, a dynamic evolution from a patent biliary tract at birth to progressive ductal obstruction and biliary cirrhosis.

Appropriate evaluations can usually exclude other specific causes of neonatal obstructive jaundice, such as specific infections, galactosemia and cystic fibrosis, but differentiation between neonatal hepatitis and EHBA may be difficult due to the histologic similarities between their resultant pathologic changes. Early diagnosis is essential, because successful biliary decompression becomes increasingly unlikely with increasing patient age. Without surgical evaluation and reconstruction, prolonged biliary hypertension causes permanent and progressive liver damage that may lead to metabolic complications, infection, sclerotizing cholangitis and cirrhosis, and may end in terminal liver insufficiency. Therefore, in the absence of findings positively securing an alternative diagnosis, biliary atresia must be excluded.

Direct and total bilirubin values, liver enzymes, alkaline phosphatase and serum levels of bile acids usually rule out infections and metabolic disorders but will not clearly distinguish EHBA from neonatal hepatitis. Imaging studies involving radiographic evaluation or ultrasound examination of the gall bladder and of extrahepatic bile ducts may be helpful but are nonspecific. The placement of a nasoduodenal tube and collection of a 24 hour sample of duodenal fluid by gravity drainage may reveal the presence of bile (bilirubin can not be measured); bile excretion is strong evidence against a diagnosis of complete biliary atresia. Such a procedure, however, is invasive. Another invasive procedure is percutaneous liver biopsy which requires interpretation by an experienced physician.

If the diagnosis is still uncertain in excluding EHBA, a laparotomy must be performed before two months of age, because infants with EHBA will develop irreversible biliary cirrhosis if the operation is deferred. Atretic bile ducts can be successfully reanastomosed in 5 to 10% of infants. EHBA is a progressive disease, and if corrective surgery is not performed prior to about eight weeks of age, there is only about a 25% chance of survival. If the corrective procedure is not performed or fails, a liver transplant becomes necessary. It is therefore critical to detect EHBA between 2–8 weeks of age.

Upon diagnosis, EHBA is surgically treated. A few patients (±15%) with EHBA have anatomic lesions which are amenable to an anastomotic procedure providing direct suture of the gut mucosa to that of a proximally patent extrahepatic biliary tree. Most patients (±85%) are not candidates for direct anastomosis. These patients had a hopeless prognosis and short life span prior to the surgical approach by Kasai of hepatoportoenterostomy which involves the direct surgical mucosa-to-mucosa anastomosis of the porta hepatis to the bowel. (Karrer et al., *Surg. Clin. North Am.* 70:1403–18 (1990) and Tagge et al., *Ann. Surg.* 214:590–8 (1991)). In cases where permanent liver damage is present, the treatment of choice is liver transplantation (Ryckman et al., *Semin. Liver Dis.* 7:134–54 (1987); Wall W. J., *Can. Med. Assoc. J.* 139:21–8 (1988); and Esquivel et al., *J. Pediatr.* 111:1039–45 (1987)).

With early diagnostic screening procedures, the number of unnecessary, early transplantations might be reduced by timely surgical intervention. In countries and areas where liver transplantation is not available, early diagnosis followed by surgical correction is the only chance of survival for patients with EHBA.

About ⅓ of all newborns appear jaundiced at birth. About ¹⁄₁₀ of these remain jaundiced after approximately 10 days. These newborns would be candidates for an EHBA diagnostic. A screening program was recently advised for EHBA in the United Kingdom. The usefulness of the screening program, however, has been sharply debated due to the lack of a simple and specific detection technology (Logan et al., *Lancet* 342:256 (1993)). Therefore, a simple and accurate non invasive test to evaluate EHBA would be invaluable to early diagnosis and treatment.

SUMMARY OF THE INVENTION

The present invention concerns a variety of assay methods for evaluating the probability of extrahepatic biliary atresia. An exemplary method involves contacting a test sample with a protease substrate reactive with dipeptidyl peptidase IV, thereby initiating a reaction; and detecting the reaction of the substrate or the formation of a detectable reaction product. The reaction or presence of the reaction product results from the presence of dipeptidyl peptidase IV in the test sample and is indicative of extrahepatic biliary atresia. The substrate may be a chromogenic substrate, and the presence of dipeptidyl peptidase IV is indicated by the production of a colored reaction product. Possible substrates include Xaa-Pro-para-nitro-analide and Xaa-Pro-coumarin, wherein Xaa is any naturally occurring or synthetic amino acid.

Another possible assay for detecting the presence of dipeptidyl peptidase IV in a test sample involves contacting the test sample with a first antibody specific for dipeptidyl peptidase IV, thereby producing antibody-bound dipeptidyl peptidase IV. The antibody-bound dipeptidyl peptidase IV is then contacted with a detection reagent, such as a protease substrate, a labeled second antibody specific for dipeptidyl peptidase IV, or a second antibody specific for dipeptidyl peptidase IV which indirectly binds a detectable label, thereby forming a detectable reaction product. The formation of a detectable reaction product results from the presence of dipeptidyl peptidase IV in the test sample and indicates the probability of extrahepatic biliary atresia.

The assays may be developed in the form of assay devices for analyzing a test sample and evaluating the probability of extrahepatic biliary atresia. In a basic form, such devices include a solid phase containing or coated with a substrate reactive with dipeptidyl peptidase IV, wherein the substrate reacts with dipeptidyl peptidase IV present in the test sample and produces a detectable reaction indicative of extrahepatic biliary atresia.

Another analytical device for determining the presence or amount of dipeptidyl peptidase IV in a test sample involves a strip of porous material having a proximal end and a distal end, wherein the test sample can travel from the proximal end to the distal end by capillary action. An antibody is immobilized in a capture site positioned between the proximal and distal ends, wherein the antibody binds dipeptidyl peptidase IV. An indicator reagent, positioned at the capture site or positioned on said strip upstream from said capture site, may be a labeled antibody which binds to dipeptidyl peptidase IV and produces a detectable signal at the capture site thereby indicating the presence or amount of dipeptidyl peptidase IV in the test sample. The device may optionally include an application pad in fluid flow contact with the proximal end of the strip, wherein the application pad receives the test sample and contains the indicator reagent. In addition, the capture reagent may be immobilized within the strip in the form of one or more discrete capture sites.

DETAILED DESCRIPTION OF THE INVENTION

The present invention involves the diagnosis of extrahepatic biliary atresia (EHBA) via the detection of elevated urinary and serum dipeptidyl peptidase IV activity levels. Dipeptidyl peptidase IV (DPPIV; E.C.N. 3.4.14.5 also known as thymocyte costimulating protein or CD26) is a protease with a very specific tissue distribution. It is located on the lumenal side of the epithelial cells lining the bile ducts (see Bristol et al., *J. Immunol.* 148:332–338 (1992) and 149:367–372 (1992)). The hypothesis leading to present invention was that if unreleased bile detergents degraded the epithelium, then DPPIV which was under pressure in the incomplete ducts may leak through the tight junctions between the cells and pass into the blood. This suggested examining the patient's blood and urine for DPPIV-like activity.

DPPIV and leucine aminopeptidase (LAP, CD 13, E.C.N. 3.4.11.2) measurements were performed on serum and urine samples of patients previously diagnosed with EHBA and of patients with jaundice due to ABO incompatibility or viral hepatitis. The results indicated the differential diagnostic potential of the assay and demonstrated that elevated DPPIV activity is indicative of EHBA. A DPPIV urine level of typically at least 1 nmol/min/ml, or more preferably of at least 2 nmol/min/ml, or a serum level of at least 15 nmol/min/ml was found to be indicative of EHBA.

The present invention, therefore, provides inexpensive and easy to perform assays for use in screening for EHBA. In addition, changes in serum levels of both LAP and DPPIV activities may be of additional help to already existing enzyme and other diagnostic tests for the differential diagnosis of EHBA. Moreover, the assays and devices of the present invention may be used to monitor patients following corrective surgery.

One embodiment of the present invention involves a chemical assay for DPPIV. The assay uses an enzyme substrate which reacts with DPPIV to form a detectable reaction product. Alternatively, the rate of the reaction of the substrate can be monitored to determine the presence or amount of DPPIV in a test sample. Suitable enzyme substrates include, but are not limited to, dipeptide substrates such as Xaa-pro-para-nitro-analide (Xaa-Pro-PNA) or Xaa-Pro-coumarin. The variable amino acid, Xaa, can be any naturally occurring or synthetic amino acid. An exemplary dipeptide substrate is Gly-Pro-para-nitro-analide (Gly-Pro-PNA). At a wavelength of 405 nanometers, the substrate has no absorbance; however, if the dipeptide substrate is cleaved (after the Pro) due to the presence of DPPIV, the formation of a reaction product can be visualized spectrophotometrically, as a yellow-green color is produced. Other substrates, such as Xaa-Pro-coumarin, can be visualized spectrofluorometrically as a fluorescent emission is produced by the reaction.

Assays embodying such reagents and reactions can be performed in any suitable reaction vessel, for example, a test tube or well of a microtiter plate. Alternatively, assay devices may be developed in disposable form such as dipstick or teststrip device formats which are well known to those skilled-in-the-art and which provide ease of manufacture and use. Such disposable assay devices may be packaged in the form of kits containing all necessary materials, reagents and instructions for use. The kits could be provided to parents of those newborns whose jaundice did not disappear after approximately 10 days. These newborns could be closely monitored by the assays of the present invention to detect the presence or amount of DPPIV in a test sample (preferably urine for home assay detection) and thereby evaluate the probability of extrahepatic biliary atresia.

Assay devices of the present invention could advantageously be formatted as dipstick or teststrip devices. For example, a dipstick may be made from a piece of bibulous material containing a chromogenic substrate for DPPIV. Alternatively, the dipstick could be made from a nonporous material on which the substrate is coated. Upon contacting the device with the desired test sample, the substrate and any DPPIV present in the sample would interact to form a detectable reaction upon the device.

In an alternative embodiment, the device may be a teststrip, wherein the substrate is contained in one or more zones along the length of a strip of bibulous material. Upon contact of one end of the strip with the desired test sample, the liquid sample migrates along the bibulous material. The reaction of the substrate and production of a detectable signal indicates the presence of DPPIV in the test sample. In a multi-zoned device, the number of discrete or isolated zones along the length of the strip which produce a detectable signal may also indicate the quantity of DPPIV present in the test sample. Alternatively, a major portion of the teststrip may contain the substrate. The length of the colored reaction formed in a teststrip having such a single, elongated substrate zone may be used to indicate the presence or amount of DPPIV in the test sample.

In an alternative assay embodiment, the rate at which the reaction occurs may be detected as an indication of the quantity of DPPIV present in the test sample. For example, the rate at which the substrate is reacted may be used to indicate the quantity of DPPIV present in the test sample. Alternatively, the rate at which the reaction product is formed may be used to indicate the quantity of DPPIV present in the test sample.

In yet another embodiment, a capture or binding assay may be performed to detect and/or quantitate the protease. For example, an antibody reactive with DPPIV protein, but which does not interfere with peptidase activity, may be immobilized upon a solid phase. The test sample is passed over the immobile antibody, and DPPIV, if present, binds to the antibody and is itself immobilized for detection. A substrate may then be added, and the reaction product may be detected to indicate the presence or amount of DPPIV in the test sample. For the purposes of the present description, the term "solid phase" may used to include any material or vessel in which or on which the assay may be performed and includes, but is not limited to, porous materials, nonporous materials, test tubes, wells, slides, etc.

In an exemplary teststrip device, a test sample application pad is optionally attached to one end of a porous strip. The strip contains an immobilized antibody which will bind to and thereby immobilize DPPIV at a predetermined site for subsequent detection. Optionally, the device may include an end of assay indicator which is positioned at the distal end of the teststrip away from the test sample contact site. The end of assay indicator produces a detectable signal upon contact with the test sample or an assay reagent thereby indicating that the assay is complete.

A test sample application pad may be a portion of the porous strip itself or a material in fluid-flow contact with the end of the porous strip, referred to as the proximal end, such that the test sample can pass or migrate from the application pad to the porous strip. Fluid-flow contact can include physical contact of the application pad to the porous strip as well as the separation of the application pad from the porous strip by an intervening space or additional material which still allows fluid to flow between the application pad and the porous strip. Substantially all of the application pad can overlap the porous strip to enable the test sample to pass through substantially any part of the application pad to the proximal end of the porous strip. Alternatively, only a portion of the application pad might be in fluid-flow contact with the porous strip. The application pad can be any material which can transfer the test sample to the porous strip.

The porous strip of the assay device can be any suitably absorbent, porous, bibulous, chromatographic or capillary possessing material through which a test sample containing the analyte can be transported by a capillary or wicking action. Natural, synthetic, or naturally occurring materials that are synthetically modified, can be used as the porous strip including, but not limited to: cellulose materials such as paper, cellulose, and cellulose derivatives such as cellulose acetate and nitrocellulose; fiberglass; cloth, both naturally occurring (e.g., cotton) and synthetic (e.g., nylon); porous gels such as silica gel, agarose, dextran, and gelatin; porous fibrous matrixes; starch based materials, such as crosslinked dextran chains; ceramic materials; films of polyvinyl chloride and combinations of polyvinyl chloride-silica; and the like. The porous strip should not interfere with the production of a detectable signal. The porous strip should have a reasonable inherent strength, or strength can be provided by means of a supplemental support.

The particular dimensions of the porous strip will be a matter of convenience, depending upon the size of the test sample involved, the assay protocol, the means for detecting and measuring the signal, and the like. For example, the dimensions may be chosen to regulate the rate of fluid migration as well as the amount of test sample to be imbibed by the porous strip.

In one possible teststrip device of the present invention, a DPPIV substrate and/or DPPIV capture antibody may be immobilized on the porous strip to form at least one analyte detection site, i.e., that region of the porous strip having one or more assay reagents non-diffusively attached thereto. In another device embodiment, the measurement or detection region of the teststrip may include a plurality of sites containing a DPPIV substrate and/or immobilized anti-DPPIV antibody. Optionally, the different detection sites may contain different amounts of substrate and/or immobilized anti-DPPIV antibody, i.e., a higher amount in the first detection site and lesser amounts in subsequent sites. For example, if 20 nanograms of antibody captures the equivalent of 1 nmol/min/ml of DPPIV, then the first detection site of a urinary assay device might contain 50 nanograms of anti-DPPIV antibody while the subsequent sites contain 10, 20, 30, etc. nanograms of antibody. Upon the addition of test sample, the number of sites displaying a detectable signal provides a quantitative indication of the amount of DPPIV present in the sample. The detection sites may be configured in any suitably detectable shape and are typically in the shape of a bar spanning the width of the teststrip.

Optionally, the multi-capture site device may be prepared such that if a threshold amount of DPPIV is not present in the test sample, then substantially all of the DPPIV will bind to the antibody in the first capture site and thus become immobilized at that site. If a greater than threshold amount of DPPIV is present in the test sample, the remaining DPPIV will bind to subsequent detection zones of immobilized antibody along the length of the teststrip. The greater the amount of DPPIV in the test sample, the greater the number of capture sites that will display a detectable signal due to the presence of DPPIV. As will be appreciated by those skilled-in-the-art, devices containing multiple DPPIV substrate sites can also be produced wherein the amount of substrate in the individual sites is designed to produce a quantitative or semiquantitative assay result.

In yet another assay embodiment, the presence or quantity of DPPIV protein may be directly detected without measuring DPPIV activity. Qualitative or quantitative immunoassays and devices may be produced with any suitable anti-DPPIV antibody (e.g., anti-CD26 antibody (TA-1) Coulter Corporation, Miami, Fla. or as produced as illustrated in Fleischer B., CD26: A surface protease involved in T-cell activation. *Immunology Today* 15:181–184 (1994)). Both polyclonal and monoclonal antibodies can be produced in accordance with methods that are well-known to and reliably used by those skilled-in-the-art.

There are several well known immunoassay methods using immunoreactants, wherein at least one of the immunoreactants is labeled with a detectable component so as to be analytically identifiable. For example, the "sandwich" or "two-site" technique may involve the formation of a ternary complex between an antigen analyte such as DPPIV and two antibodies. A convenient method of detecting complex formation in such a technique is to provide one labeled antibody and an unlabeled antibody bound to a solid phase support such that the complex can readily be isolated. In this example, the amount of labeled antibody associated with the solid phase is directly proportional to the amount of analyte in the test sample.

An alternative technique is the "competitive" assay. In one example of a competitive assay, the capture mechanism again may use an antibody attached to an insoluble solid phase, but a labeled reagent (rather than a labeled antibody) competes with the analyte present in the test sample for binding to the immobilized antibody. Similarly, an immobilized reagent can compete with the analyte of interest for a labeled antibody. In these competitive assays, the quantity of captured labeled reagent is inversely proportional to the amount of analyte present in the sample.

Examples of devices based upon these principles include those described in the following patents and patent applications. Deutsch et al. describe a chromatographic teststrip device in U.S. Pat. Nos. 4,094,647, 4,235,601 and 4,361,537. The device comprises a material capable of transporting a solution by capillary action. Different areas or zones in the strip contain the reagents needed to perform a binding assay and to produce a detectable signal as the analyte is transported to or through such zones. The device is suited for chemical assays as well as binding assays which are typified by the binding reaction between an antigen and a complementary antibody.

Many variations on the device of Deutsch et al. have been subsequently disclosed. For example, Tom et al. (U.S. Pat. No. 4,366,241) disclose a bibulous support with an immunosorbing zone, containing an immobilized specific binding member. The test sample is applied to the immunosorbing zone, and the assay result is read at the immunosorbing zone.

Weng et al. (U.S. Pat. Nos. 4,740,468 and 4,879,215) also describe a teststrip device and methods for performing a binding assay. The device is used with a test solution containing the test sample, suspected of containing the analyte of interest, and a labeled specific binding member which binds to the analyte. Greenquist et al. (U.S. Pat. Nos. 4,806,311 and 4,806,312) describe a layered assay device for performing binding assays similar to those of Weng et al.

The term "label", as used herein, refers to any substance which directly or indirectly attaches to another binding member assay reagent or analyte and which is capable of producing a signal that is detectable by visual or instrumental means. Various suitable labels for use in the present invention can include chromogens; catalysts; fluorescent compounds; chemiluminescent compounds; radioactive labels; direct visual labels including colloidal metallic and non-metallic particles, dye particles, enzymes or substrates, or organic polymer latex particles; liposomes or other vesicles containing signal producing substances; and the like. The label may indirectly attach to an antibody specific for DPPIV by means of additional ligands such as avidin/biotin. For example, a biotinylated antibody may bind an avidin/label reagent which binds to the biotinylated antibody before or after the antibody binds to DPPIV.

Rosenstein (European Patent Office Publication No. 0 284 232) and Campbell et al. (U.S. Pat. No. 4,703,017) describe assay methods and devices for performing specific binding assays, wherein the preferred detectable label is a colored particle consisting of a liposome containing a dye. Bahar, et al. (U.S. Pat. No. 4,868,108) describe an assay method and device for performing a specific binding assay, wherein the device involves a multizoned support. Eisinger et al. (U.S. Pat. No. 4,943,522) describe an assay method and a device for performing specific binding assays, using a multizoned large-pored lateral flow membrane through which test sample is transported by capillary action.

Hochstrasser (U.S. Pat. No. 4,059,407) discloses a dipstick device which can be immersed in a biological fluid for a semi-quantitative measurement of the analyte in the fluid. The semi-quantitative measurement of the analyte is accomplished by using a series of reagent-containing pads, wherein each pad in the series will produce a detectable color (i.e., a positive result) in the presence of an increasing amount of analyte. Also of interest in the area of dipstick devices are U.S. Pat. Nos. 3,802,842, 3,915,639 and 4,689,309.

Grubb et al. (U.S. Pat. No. 4,168,146) describe the use of a porous teststrip material to which an antigen-specific antibody is immobilized by covalent binding to the strip. The teststrip is immersed in a solution suspected of containing an antigen, and capillary migration of the solution up the teststrip is allowed to occur. Variations on such a teststrip are disclosed in U.S. Pat. No. 4,435,504 which employs a two enzyme indicator system; U.S. Pat. No. 4,594,327 which discloses the addition of a binding agent to whole blood samples which causes the red blood cells to aggregate at the area of the strip adjacent to the air/liquid interface; and U.S. Pat. No. 4,757,004 which discloses a means for controlling the shape of the fluid front migrating along the teststrip. The assay principle is further described in Zuk et al., Enzyme Immunochromatography—A Quantitative Immunoassay Requiring No Instrumentation, *Clinical Chemistry*, 31 (7): 1144–1150 (1985).

Further examples of strip-type diagnostic devices include the following. Swanson et al. (EP 88 636) describe an apparatus for the quantitative determination of an analyte involving a fluid-permeable solid medium containing a predetermined number of successive spaced reaction zones. Freisen et al. (U.S. Pat. No. 4,861,711) describe a sheet-like diagnostic device containing several functional sectors through which the sample must pass. At least one of the sectors includes an immobilized reagent having a biological affinity for the analyte or an analyte complex.

Also of interest in the area are Tanswell et al. (U.S. Pat. No. 4,642,930), Valkirs et al. (U.S. Pat. No. 4,727,019), Wolters et al. (U.S. Pat. No. 4,343,896), and Parikh et al. (U.S. Pat. No. 4,298,685), Gordon et al. (U.S. Pat. No. 4,956,302), Gordon et al. (U.S. Pat. No. 4,960,691) and Bolz et al. (U.S. Pat. No. 4,020,151).

As will be appreciated from this description of possible device formats, there is significant activity in the field of disposable assay devices. There is a growing demand for devices that require few or no manipulative steps to perform the desired assay, for devices that can be used by relatively untrained personnel, and for devices that provide results which are minimally affected by variations in the manner in which the assay is performed. Further considerations are the ease with which the resultant detection signal may be observed as well as the ease with which any signal substance immobilized at the detection site can be distinguished from the signal substance which passed through the detection site.

The following assay results describe dipeptidyl peptidase IV and CD13 leucine/neutral amino-peptidase (LAP, E.C.N. 3.4.11.2) measurements in diagnosing EHBA. DPPIV and CD13 LAP are large membrane-associated proteins (approximately 100 kD) expressed in the liver on bile canaliculi and biliary epithelium, on the surface of gut epithelium and on some kidney canaliculi, as well as on cells of hematopoietic origin.

The results demonstrate the utility of the DPPIV test as a procedure for the detection of EHBA. The use of urinary DPPIV measurements, as well as the routine physical examination of the patient and study of stool and urine for signs of jaundice, provides a useful screening procedure for EHBA. Patients with high urinary DPPIV activity may be further tested for serum enzymes. The number of EHBA-suspect patients at this point should be low enough not to overload radiological, ultrasonographic and histological (biopsy) diagnostic capacity of pediatric hospitals, thereby ensuring early diagnosis and treatment of EHBA.

EXAMPLES

Example 1

Detection of DPPIV

DPPIV and LAP activities were measured in urine and serum samples of known EHBA patients. Assays were performed six times prior to surgery. The patients (average age: 8 weeks) had been admitted to the hospital because of persistent jaundice. All of the cases had been histologically diagnosed by needle biopsies.

Enzyme activities were measured in triplicates at 24° C., by mixing 100 μl or 50 μl of sample to 100 μl or 150 μl of a reaction buffer (DPPIV or LAP, respectively) containing 200 μM of chromogenic substrate in 0.1M Tris buffered Triton X-100 (0.1% v/v) at pH:7. The substrates were Gly-Pro-PNA (for DPPIV and Leu-PNA for LAP (both materials are commercially available from Bachem, San Diego, Calif.).

The mixtures were incubated for 30 minutes in 96-well microplates. Optical density readings were taken four times during incubation with a 405 nm filter in an ELISA reader, according to the manufacturer's instructions. Enzyme activity was expressed in nmol/min/ml based on the progression curve calculated from the concentration of hydrolyzed substrates. Purified DPPIV may be used as a positive control against which to compare the DPPIV assay results. Purified DPPIV may be made in accordance with the method described in Bristol et al., *J. Immunol.* 149:367–372 (1992). Reaction buffer, without substrate, served as the negative control. The negative control did not show an increase in the concentration of hydrolyzed substrate, suggesting that the substrates were stable in the assay.

Fifty healthy volunteers provided urine samples for the initial control studies. All volunteers had been tested for creatinine in the urine and showed normal values. Urinary enzyme activities were not corrected, because of the very low level of enzyme activity present in normal urine. In addition to the healthy volunteers, urine and blood samples were collected from five age-matched healthy neonates (with parental consent). For comparison with EHBA patients, LAP and DPPIV measurements were performed on serum and urine samples from four neonates with jaundice due to ABO incompatibility and from sixteen (average age: 9.5 years) with viral hepatitis. Routine laboratory tests included GTP, GOT, γGT, AP and bilirubin measurements. Statistical analysis was performed with Sigma Plot 5.0 (Jandel Scientific Corporation, San Rafael, Calif.)

Figure 1:
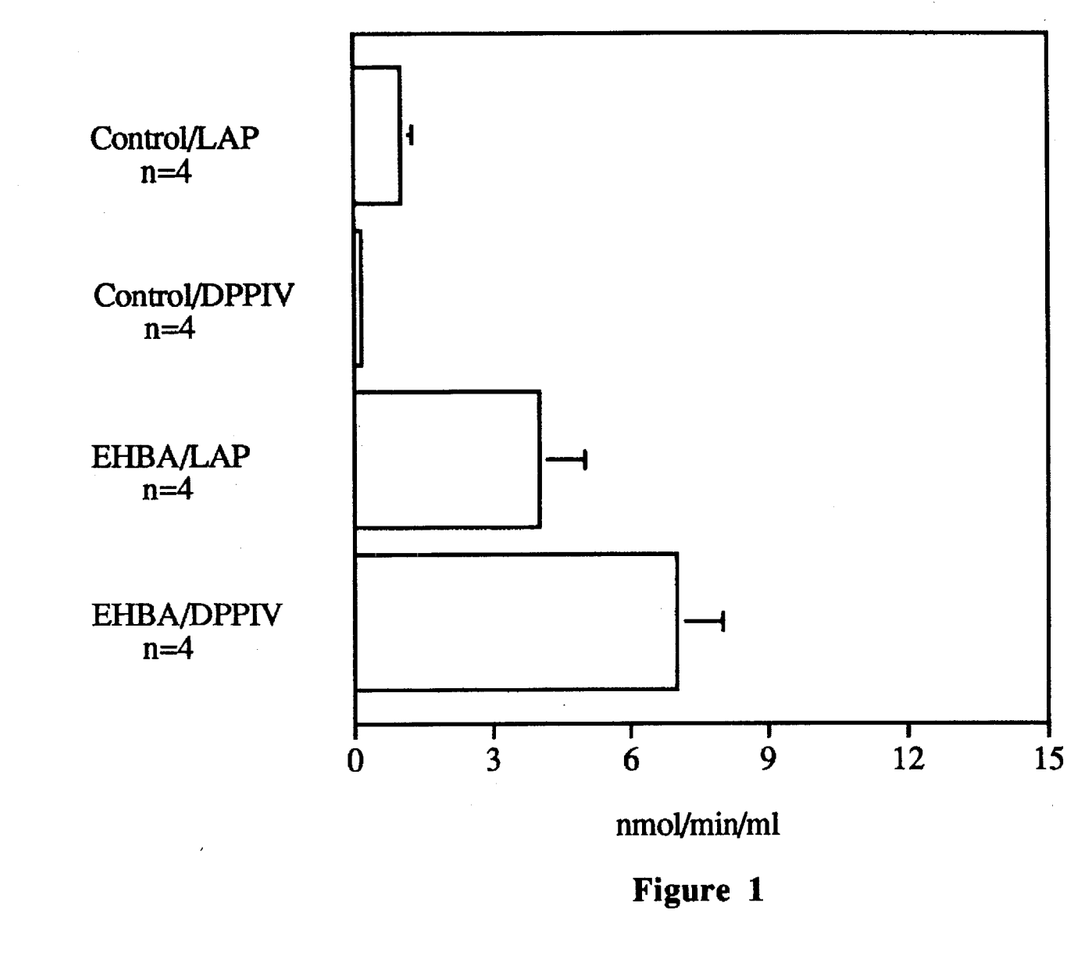
FIG. 1 depicts dipeptidyl peptidase IV and leucine aminopeptidase activities in urine samples of control and EHBA patients.

The urinary DPPIV and LAP activity of the 50 normal young volunteers (average age: 27 years) were 0.199±0.224 nmol/min/ml and 0.078±0.272 nmol/min/ml, respectively. The four urine samples from age-matched controls showed low or barely detectable activity (0.06±0.05 nmol/min/ml for DPPIV and 0.820±0.215 nmol/min/ml for LAP). EHBA patients had 6.927±3.45 nmol/min/ml and 8.52±13.05 nmol/min/ml urinary activities for DPPIV and LAP, respectively, with DPPIV differing significantly ($p<0.05$) from control. FIG. 1 depicts the urinary DPPIV activity of age-matched control and EHBA patients. Measurements in the EHBA group were performed six times. The number of patients in each group is indicated (urine samples of two patients were measured two times). The horizontal bars indicate the standard error. A single high value (over 15 nmol/min/ml) of LAP activity is offscale on the figure.

Figure 2:
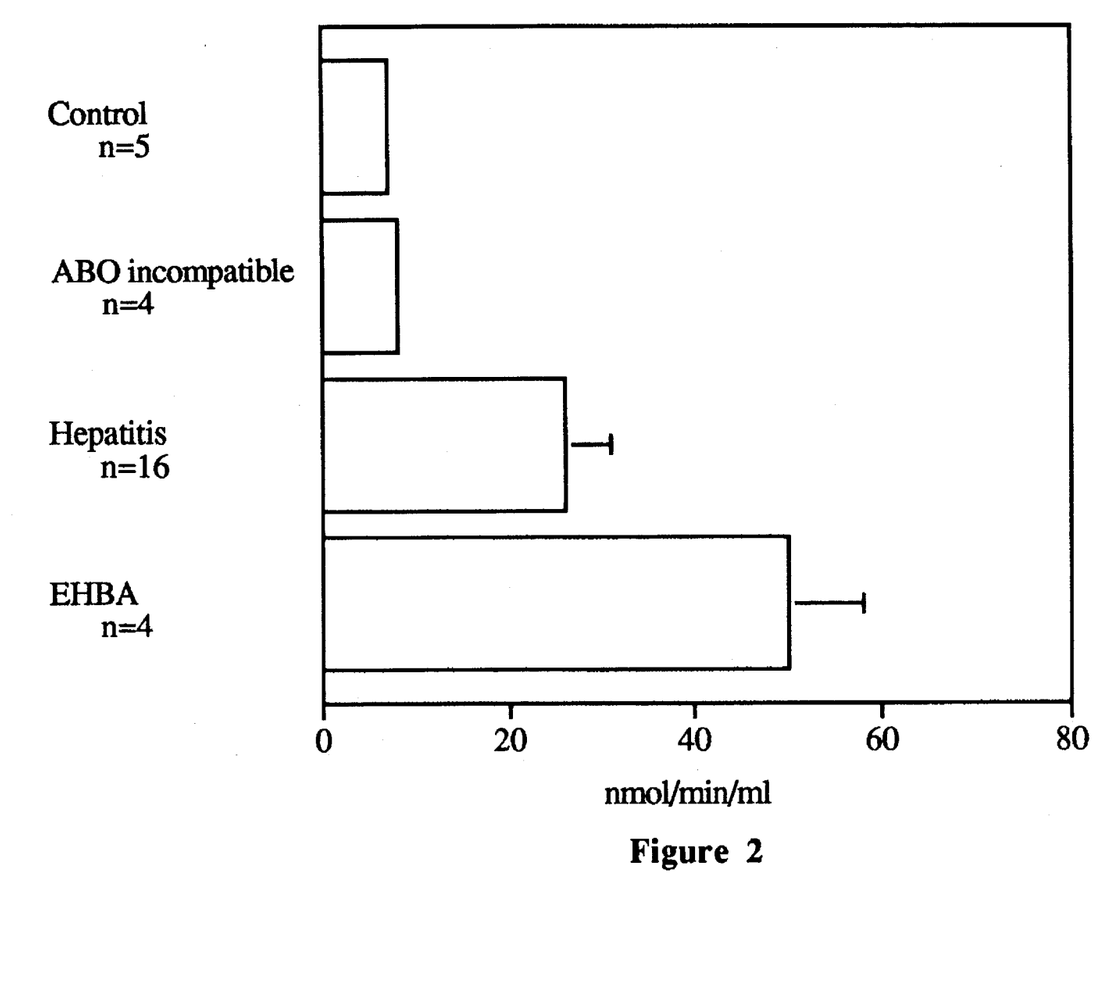
FIG. 2 depicts dipeptidyl peptidase IV activity in serum samples.
Figure 3:
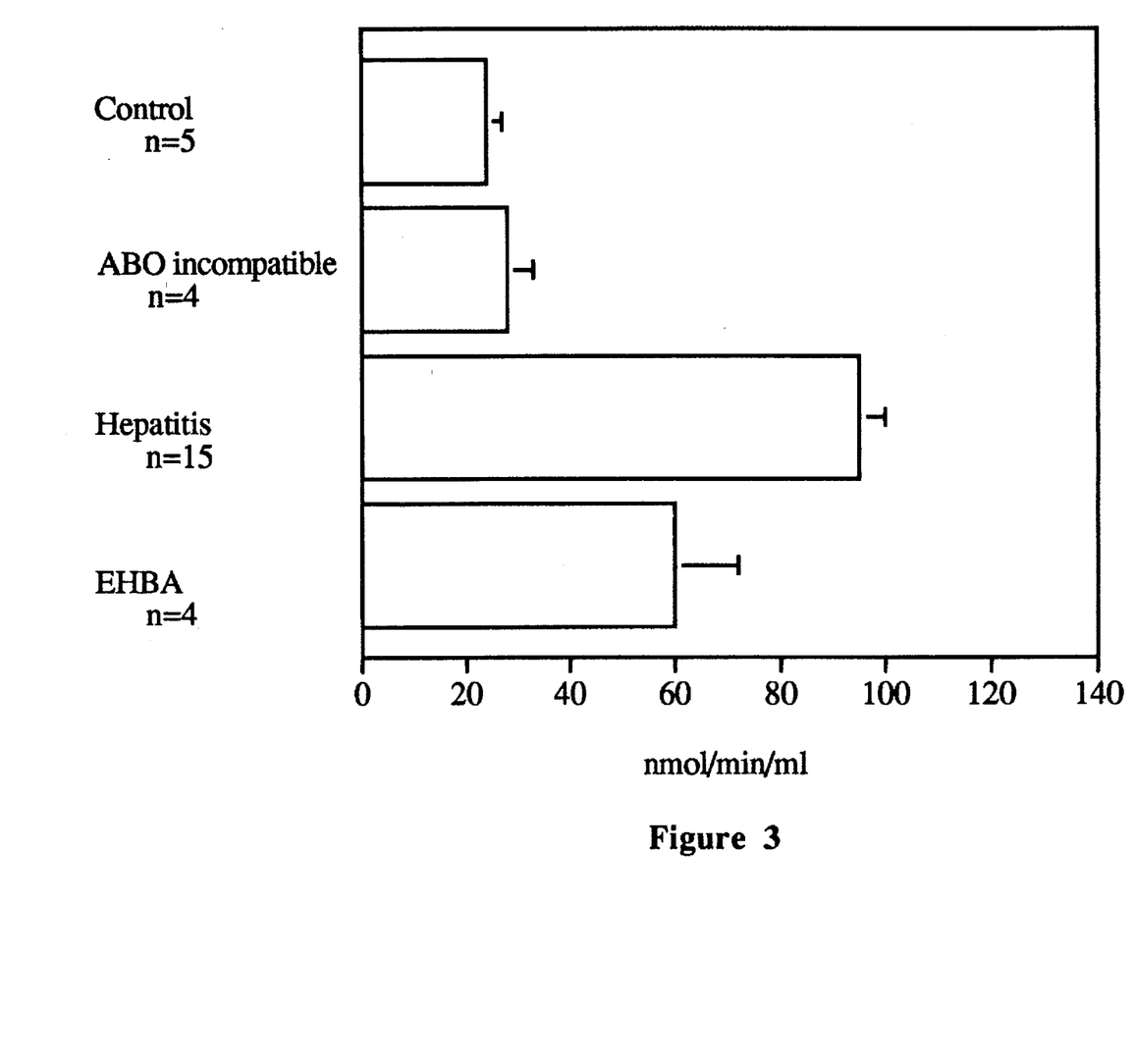
FIG. 3 depicts leucine aminopeptidase activity in serum samples.

When serum DPPIV activity was compared between the controls and different disease groups (FIG. 2), it became clear that EHBA patients had significantly higher DPPIV activity ($p<0.05$) than normal, as well as higher DPPIV activity than patients with jaundice due to ABO incompatibility. Viral hepatitis patients presented two groups; one with values as low as the control (7 of 16 patients) and another with DPPIV activity (24–60 nmol/min/ml) values as high as the EHBA patients. Compared to controls, LAP activity was significantly elevated ($p<0.05$) in hepatitis patients and slightly elevated in three of four EHBA patients. FIG. 3 illustrates the serum LAP activity measurements. A comparison of normal control and different disease groups is indicated. Measurements in the EHBA group were done seven times. The number of patients in each group is indicated, and the horizontal bars indicate the standard error.

These results illustrate that urinary measurement of DPPIV activity provides a method of screening for EHBA. DPPIV levels of at least 1–3 nmol/min/ml indicate EHBA. Elevated DPPIV levels in serum, when compared to LAP and other enzymes, have a potential differential diagnostic value, e.g., GPT and LAP activities are higher in viral hepatitis than in EHBA patients (data not shown).

CD26, DPPIV and CD13 LAP are large membrane-associated proteins (approximately 100 kD) expressed in the liver on bile canaliculi and biliary epithelium, on the surface of gut epithelium and on some kidney canaliculi, as well as on cells of hematopoietic origin. The enzymes present in the serum are probably processed forms and most likely have considerably lower molecular masses. Elevated serum levels show good linear correlation with elevated urinary levels for both enzymes ($r_{LAP}=0.843$, $r_{DPPIV}=0.87$) suggesting that the serum enzyme can be filtered or that it is secreted into the urine. Since both enzymes are expressed in kidney canaliculi, urinary infections may represent a differential diagnostic problem when high levels of DPPIV or LAP are measured in the urine.

Example 2

DPPIV Dipstick Assay

A chromogenic substrate, such as Gly-Pro-PNA, is applied to a strip of filter paper and dried. The amount of substrate may be predetermined such that the reaction with DPPIV will produce a visually detectable reaction, e.g., approximately 80 nmol/cm$^2$ of substrate/reaction site may be used. The tip of the paper is subsequently contacted with a urine sample. If the test sample contains DPPIV, the substrate reacts with the DPPIV and produces a detectable change in color.

Example 3

DPPIV Teststrip Assay

A chromogenic substrate (Gly-Pro-PNA, 80 nmol/cm$^2$) is applied to and dried in one or more isolated zones in the form of bars across the width of an elongated strip of filter paper. The tip of the paper is subsequently contacted with an fluid test sample such as serum or urine. The sample wicks through the test strip, thereby contacting the isolated substrate. If the test sample contains DPPIV, the substrate reacts with the DPPIV and produces a detectable change in color in one or more of the detection zones. By varying the amount of substrate present in the individual zones, the production of a detectable signal may be quantitative.

Example 4

DPPIV Teststrip Device

In the present invention, binding assays may involve the specific binding of DPPIV and/or an indicator reagent (comprising a label directly or indirectly attached to an antibody specific for DPPIV) to a capture reagent (comprising a second anti-DPPIV antibody). The capture reagent immobilizes DPPIV on a chromatographic material or at least slows the migration of the analyte or indicator reagent through the chromatographic material.

The label, as described above, allows the indicator reagent to produce a detectable signal that is related to the presence or amount of analyte in the test sample. The selection of a particular label is not critical, but the label will be capable of generating a detectable signal either by itself, such as a visually detectable signal generated by colored organic polymer latex particles, or in conjunction with one or more additional signal producing components, such as an enzyme/substrate signal producing system.

The capture reagent, in the DPPIV assay, is used to facilitate the observation of the detectable signal by substantially separating DPPIV and/or the indicator reagent from other assay reagents and the remaining components of the test sample. Typically, the capture reagent is immobilized on the chromatographic material to form a "capture site", i.e., a region of the chromatographic material having one or more capture reagents non-diffusively attached thereto.

The assay device may include a chromatographic material having a proximal end and a distal end, wherein the test sample can travel from the proximal to the distal end by capillary action. The chromatographic material contains the capture reagent, i.e., anti-DPPIV antibody, which is immobilized in a capture site and which is capable of binding to DPPIV. An optional test sample application pad may be provided in fluid flow contact with the proximal end of the chromatographic material. The application pad may be used to receive the test sample and pass the sample to the chromatographic material. The application pad may optionally contain a diffusive indicator reagent capable of migrating from the application pad to the chromatographic material. The indicator reagent is preferably capable of binding to DPPIV, e.g., a labeled second anti-DPPIV antibody. The binding of the indicator reagent to DPPIV results in the formation of a ternary or sandwich complex and a detectable signal at the capture site, thereby indicating the presence or amount of DPPIV in the test sample.

The capture reagent can be positioned upon or within the chromatographic material in a variety of configurations. In alternative embodiments, the capture reagent can be distributed in any pattern convenient for detection including, but not limited to, bars, stripes, numerals, letters, dots and symbols such as "+/–", "%" or the like which display the detectable signal upon completion of the assay.

The assay method is easily performed by placing a test sample suspected of containing the analyte onto the application pad, thereby contacting the indicator reagent. The test sample and the indicator reagent are transferred to the chromatographic material, and migrate through the chromatographic material to contact the capture reagent, resulting in production of a detectable signal at the capture site.

The foregoing descriptions of the specific embodiments so fully reveal the general nature and applicability of the present invention that others can readily modify, adapt and/or optimize such specific embodiments for an assortment of assay methods and devices, using a variety of reagents and materials, without departing from the present inventive concept. Any such modifications and adaptations are intended to be embraced within the meaning and range of equivalents of this invention. It is also to be understood that the phraseology and terminology employed herein are for the purpose of description and not of limitation. All articles, applications and patents contained in this description of the present invention are incorporated by reference.

What is claimed is:

1. A method of screening for extrahepatic biliary atresia, the method comprising the steps of:
   a) contacting a test sample to an antibody specific for dipeptidyl peptidase IV thereby producing antibody-bound dipeptidyl peptidase IV;
   b) contacting said antibody-bound dipeptidyl peptidase IV with a protease substrate reactive with dipeptidyl peptidase IV, thereby initiating a reaction; and
   c) detecting the reaction of said substrate or the formation of a detectable reaction product, wherein the reaction or presence of the reaction product results from the presence of dipeptidyl peptidase IV in the test sample and is correlated with extrahepatic biliary atresia.

2. The method according to claim 1, wherein said substrate is a chromogenic substrate and the presence of dipeptidyl peptidase IV is indicated by the production of a colored reaction product.

3. The method according to claim 1, wherein said substrate is selected from the group consisting of Xaa-Pro-para-nitro-analide and Xaa-Pro-coumarin, wherein Xaa is any naturally occurring or synthetic amino acid.

4. The method according to claim 3, wherein said substrate is Gly-Pro-para-nitro-analide.

5. A method according to claim 1, wherein said test sample is a urine sample, and wherein the presence of dipeptidyl peptidase IV in an amount of at least 1 nmol/min/ml is correlated with extrahepatic biliary atresia.

6. A method according to claim 1, wherein said test sample is a serum sample, and wherein the presence of dipeptidyl peptidase IV in an amount of at least 15 nmol/min/ml is correlated with extrahepatic biliary atresia.

7. An assay for detecting the presence of dipeptidyl peptidase IV in a test sample, wherein the presence of dipeptidyl peptidase IV is correlated with extrahepatic biliary atresia, the assay comprising the steps of:
   a) contacting the test sample with a first antibody specific for dipeptidyl peptidase IV, thereby producing antibody-bound dipeptidyl peptidase IV;

b) contacting the antibody-bound dipeptidyl peptidase IV with a detection reagent selected from the group consisting of a protease substrate, a labeled second antibody specific for dipeptidyl peptidase IV, and a second antibody specific for dipeptidyl peptidase IV which indirectly binds a detectable label, thereby forming a detectable reaction product; and c) detecting the formation of said detectable reaction product resulting from the presence of dipeptidyl peptidase IV in the test sample.

8. The assay according to claim 7, wherein said detection reagent is a protease substrate selected from the group consisting of Xaa-Pro-para-nitro-analide and Xaa-Pro-coumarin, wherein Xaa is any naturally occurring or synthetic amino acid.

9. The assay according to claim 7, wherein said detection reagent is a labeled anti-dipeptidyl peptidase IV antibody.

10. The assay according to claim 7, wherein said first antibody is immobilized in an isolated site of a dipstick or teststrip.

11. An assay device for analyzing a test sample and screening for extrahepatic biliary atresia, comprising: a solid phase containing an antibody reactive with dipeptidyl peptidase IV immobilized in a capture site; a substrate reactive with dipeptidyl peptidase IV at said capture site, wherein said substrate reacts with dipeptidyl peptidase IV present in the test sample and produces a detectable reaction correlated with extrahepatic biliary atresia.

12. The device according to claim 11, wherein said substrate is a chromogenic substrate and the presence of dipeptidyl peptidase IV is indicated by the production of a colored reaction product.

13. The device according to claim 11, wherein said substrate is selected from the group consisting of Xaa-Pro-para-nitro-analide and Xaa-Pro-coumarin, wherein Xaa is any naturally occurring or synthetic amino acid.

14. The device according to claim 11, wherein said solid phase is in the form of an elongated strip of porous material.

15. An analytical device for determining the presence or amount of dipeptidyl peptidase IV in a test sample, comprising:

a strip of porous material having a proximal end and a distal end, wherein the test sample can travel from said proximal end to said distal end by capillary action;

an antibody immobilized in a capture site positioned between said proximal and distal ends, wherein said antibody specifically binds dipeptidyl peptidase IV;

an indicator reagent at said capture site or positioned on said strip upstream from said capture site, wherein said indicator reagent is a labeled antibody which specifically binds to dipeptidyl peptidase IV and produces a detectable signal at said capture site thereby indicating the presence or amount of dipeptidyl peptidase IV in the test sample.

16. The device according to claim 15, further comprising an application pad in fluid flow contact with said proximal end of said strip, wherein said application pad receives the test sample and contains said indicator reagent.

17. The device according to claim 15, wherein said capture reagent is immobilized within said strip to form at least one discrete capture site.

18. The device according to claim 15, wherein said capture reagent is immobilized within said strip in the form of two or more separate capture sites.

* * * * *

UNITED STATES PATENT AND TRADEMARK OFFICE
CERTIFICATE OF CORRECTION

PATENT NO.    : 5,601,986
DATED         : February 11, 1997
INVENTOR(S)   : Laszlo, Takacs It is certified that error appears in the above-identified patent and that said Letters Patent is hereby corrected as shown below:

Column 9,
Line 63: Between "sixteen" and "(average age:", insert -- children --.

Column 11,
Line 51: Between "proximal" and "to", insert -- end --.

Signed and Sealed this

Twenty-first Day of August, 2001

*Attest:*

NICHOLAS P. GODICI
*Attesting Officer*    *Acting Director of the United States Patent and Trademark Office*